United States Patent [19]

Hamann et al.

[11] Patent Number: 5,371,251
[45] Date of Patent: Dec. 6, 1994

[54] POLYOL POLYETHER SULFOSUCCINATES, A PROCESS FOR PREPARING THEM, AND THEIR USE

[75] Inventors: Ingo Hamann, Bad Orb; Elke Hohn; Hans-Jürgen Köhle, both of Schlüchtern, all of Germany

[73] Assignee: Witco GmbH, Bergkamen, Germany

[21] Appl. No.: 957,430

[22] Filed: Oct. 5, 1992

[30] Foreign Application Priority Data

Nov. 7, 1991 [DE] Germany .............................. 4136579

[51] Int. Cl.$^5$ .................................................. C11D 1/29
[52] U.S. Cl. .......................................... 554/97; 554/96; 554/115; 554/121; 554/122; 554/149; 554/158; 554/85
[58] Field of Search ........................ 554/85, 97, 96, 99, 554/115, 121, 122, 149, 158

[56] References Cited

U.S. PATENT DOCUMENTS

| | | | |
|---|---|---|---|
| 3,640,998 | 2/1972 | Mansfield et al. | 260/210 |
| 4,064,244 | 12/1977 | Sorg | 514/371 |
| 4,241,072 | 12/1980 | Bolhofer | 514/252 |
| 4,250,050 | 2/1981 | Asbeck et al. | 252/354 |
| 4,517,196 | 5/1985 | Schlecker et al. | 544/245 |
| 4,992,263 | 2/1991 | Tesmann et al. | 424/63 |

FOREIGN PATENT DOCUMENTS 0190779  4/1989  European Pat. Off. .
2700072  7/1978  Germany .

OTHER PUBLICATIONS

Cuntze et al, Chemical Abstracts, vol. 92, #26, 217060d, abstract of DE 2,840,113.

Chem. Abstracts, vol. 75(21), Abst. No. 129,703-J dated Nov. 22, 1971.
Otey et al., The Journal of the American Oil Chemists' Society, vol. 38, Oct., 1961, pp. 517–520.

*Primary Examiner*—José G. Dees
*Assistant Examiner*—Deborah D. Carr
*Attorney, Agent, or Firm*—Curtis, Morris & Safford

[57] ABSTRACT

The invention relates to fatty acid monoglyceride polyglycol ether sulfosuccinates of the general formula

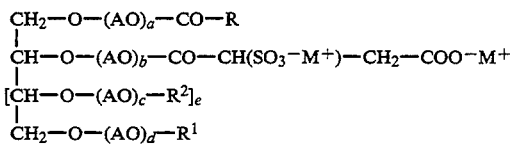

where
R represents a straight-chain or branched alkyl or alkylene group having from 7 to 21 carbon atoms;
$R^1$ represents H or CO—R;
$R^2$ may represent, independently of each other, H or the group —CO—CH($SO_3^-M^+$)—CH$_2$—COO$^-M^+$;
A represents the same or different and each is an alkylene group having from 2 to 3 carbon atoms;
a,b,c,d may be the same or different, from 0 to 5,
e being from 1 to 3,
f is a multiplication product of c times e, and
a+b+f+d is from 2 to 25; and
$M^+$ represents an alkali-metal ion or an ammonium ion, and to their preparation and use.

5 Claims, No Drawings

POLYOL POLYETHER SULFOSUCCINATES, A PROCESS FOR PREPARING THEM, AND THEIR USE

The invention relates to new polyol polyether sulfosuccinates, a process for preparing them, and their use as cleaning agents and in cosmetic preparations.

Cosmetic preparations, and particularly those in the hair- and body-cleaning area, such as shower baths, bubble baths, hair shampoos and liquid soaps, contain as cleaning ingredients mainly anionic surface-active agents (surfactants) such as carboxylates, alkyl sulfates and alkyl ether sulfates, and sulfosuccinates.

These preparations are intended to clean the skin surface, and preferably just the film adhering to it, which may be formed by excretions such as perspiration and oils, skin flakes, or dirt deposited from the environment. The cleaner should not leach out the skin, irritate it, or impair its natural functions.

But since the frequent, and in the last few years almost daily, use of these preparations may result in irritation of the skin, they often incorporate so-called mild surfactants, such as betaines, protein derivatives, ampholytes, alkyl ether carboxylates and sulfosuccinates, to improve their tolerance by the skin and the mucosa of the eye.

Baby-care products and baby shampoos in particular should contain extremely low levels of substances irritating the skin and the mucosa of the eye. While the irritating effect of anionic surfactants, conventionally used because of their excellent cleaning and foaming properties, can be considerably reduced with the known mild co-surfactants, there is room for improvement, especially so far as their tolerance by the mucosa of the eye is concerned.

When used in high concentrations or alone, mild surfactants are largely nonirritating, but their cleaning and foaming properties fall short of meeting practical requirements and their viscosities are not satisfactory.

Another criterion for the usability of surfactants is their toxicity. The toxicity may reside in the surfactants themselves or in products formed by them through interaction with the ingredients of the formulation.

For example, the fatty alkanolamides, which used to be favored because of their advantageous end-use and skincare properties, are now employed only reluctantly in cosmetic preparations since the residual content of free diethanolamine remaining in the manufacturing process cannot be eliminated and may lead to nitrosamine formation. (See European patent publication 0 306 843.) N-nitrosamines have proved to be carcinogenic in experiments with animals.

Moreover, because of the growing environmental consciousness, products are demanded which are derived from renewable natural resources, do not exhibit any toxicity, and can be decomposed in municipal sewage-treatment plants rapidly and completely without toxic intermediate products forming.

While the well-established products based on polyhydric alcohols, such as the glycerol-based monofatty acid ester and/or difatty acid ester alkoxylates, have low toxicity and are mild products which do not irritate the skin, their cleaning action fails to satisfy practical requirements.

The object of the present invention is to overcome these drawbacks of the prior art and to provide cleaning agents for household and industry and cosmetic preparations that are mild and readily tolerated by the skin, and particularly preparations in the hair- and body-cleaning area.

This object is accomplished through the concurrent use in accordance with the invention of sulfosuccinates based on polyols containing alkoxylated ester groups and having more than three hydroxyl groups per mol. The invention has as its subject polyol polyether sulfosuccinates of the general formula

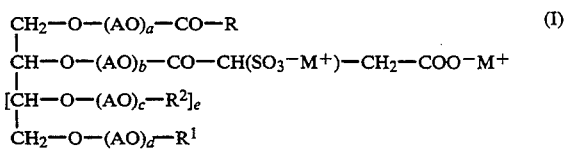

where
R represents a straight-chain or branched alkyl or alkylene group having from 7 to 21 carbon atoms;
$R^1$ represents H or $-CO-R$;
$R^2$ may represent, independently of each other, H or the group $-CO-CH(SO_3^-M^+)-CH_2-COO^-M^+$;
A represents the same or different alkylene groups having from 2 to 3 carbon atoms;
a, b, c, d may be the same or different, from 0 to 5, e is from 1 to 3 and,
f is a multiplication product of c times e ($c \cdot e$ or $c \times e$) and, $a+b+f+d$ being from 2 to 25; and
$M^+$ represents an alkali-metal ion or an ammonium ion.

The invention also has as a subject a process for preparing compounds of the general formula (I).

The invention further has as subjects aqueous hair-cleaning and hair-care preparations, rinses, and skincare and skin-cleansing preparations which are characterized in that they contain from 1 to 10 parts by weight of at least one of the compounds of the general formula (I); given amounts of at least one surfactant from the group of nonionic, amphoteric, zwitterionic and nonionic surfactants; preferably from 0.1 to 30 parts by weight, and optionally from 0.1 to 15 parts by weight, of one of the commonly used agents from the group of additives and aids, thickeners, fragrances, preservatives, dyes and plant extracts; and optionally sufficient water to make 100 parts.

Further subjects of the invention are characterized by the claims.

The alcohols used in the preparation of the compounds of the invention are polyol compounds with more than three hydroxyl groups. These are preferably commercial sugar alcohols such as erythritol, xylitol, and particularly the hexahydric reduction products of the monosaccharides, such as mannitol and sorbitol. Depending on the requirements to be met by the end product, they may be a highly purified grade or of commercial technical-grade purity.

In accordance with the invention, the process is generally conducted by preparing in a first step the polyol alkoxylates by adding alkylene oxides such as ethylene oxide or propylene oxide to the polyols in the presence of a basic catalyst at temperatures of from 120° to 180° C.; by preparing in a second step the polyol alkoxylate fatty acid esters by esterification or transesterification with fatty acids or fatty acid esters at temperatures of from 120° to 180° C., optionally in the presence of a catalyst; by preparing in a third step, by adding maleic anhydride at temperatures of from 60° to 80° C. the half ester; and by reacting the latter in a final step at temperatures of from 60° to 80° C. with aqueous sodium sulfite solution to give the salt of the corresponding sulfonic acid. (See J. Amer. Oil Chem. Soc., 38, 517–520 [1961]; U.S. Pat. No. 3,640,998.)

The compounds of the invention have degrees of alkoxylation with a, b, c and d of from 0 to 5 and preferably 1 to 3 each, e is from 1 to 3, f is the multiplication product of c times e (c×e or c·e), and a+b+f+d being from 2 to 25, and preferably from 5 to 20. These values should be regarded as statistical mean values.

The fatty acids used are monobasic acids or their alkyl esters with from 8 to 22, and preferably from 12 to 18, carbon atoms, and preferably the naturally occurring ones, such as lauric acid, palmitic acid, stearic acid, oleic acid, linoleic acid, linolenic acid, ricinoleic acid and coconut acid or mixtures thereof. (See J. Am. Oil Chem. Soc. 38, 517–520 (1961) and European patent publication 0 190 779.)

The reaction giving the sulfosuccinate is carried out with maleic anhydride, followed by sulfonation with sodium sulfite by methods which are known per se. (See German patent publication OS 2 700 072.)

The mixture containing one mol of maleic anhydride per mol of hydroxyl group to be reacted is stirred at 60°–80° C. until the anhydride has completely reacted. The maleic half-ester is then introduced into an aqueous sodium sulfite solution (one equivalent of sulfite per equivalent of half-ester) and sulfonated at temperatures of from 60° to 80° C. until the sulfite has been reacted completely. The pH of the aqueous product is then adjusted to neutral.

The compounds of the invention are represented by the formula (I) in idealized form. The technical-grade mixtures contain, in addition to the desired esters, minor amounts of compounds with a different degree of esterification. The degrees of alkoxylation indicated are statistical mean values.

Purification is not necessary for the use in accordance with the invention, that is, the technical-grade mixtures can be used as is.

The inventive mixtures for cleaning purposes and cosmetics are generally in the form of aqueous mediums or of aqueous alcoholic solutions, cremes, emulsions or gels, and to adapt them to the intended end use they may incorporate the aids and additives commonly used in the manufacture of cleaning agents and cosmetic preparations in the hair- and body-cleaning area, that is, shower baths, bubble baths, shampoos, liquid soaps, baby care and washing products, as well as for mild cleaners such as hand dish-washing compounds, neutral cleaners and all-purpose cleaners.

For cosmetic uses, the surfactants, fragrances, preservatives, dyes, plant extracts, etc., and other cosmetic additives commonly used in this field may be employed.

Suitable surfactants for the cleaning formulations are, in addition to the known betaines, amphoteric and nonionic compounds, and particularly anionic surfactants such as carboxylates, alkyl sulfates, alkyl ether sulfates, alkyl sulfonates, alkyl ether sulfonates and alkyl sulfosuccinates. Preferred are, in accordance with the invention, alkylamidobetaines such as REWOTERIC® [1] AM B 13 and AM B 14, carboxyglycinates such as REWOTERIC® AM 2 C NM, carboxypropionates such as REWOTERIC® AM KSF 40, sulfobetaines such as REWOTERIC® AM CAS, anionic surfactants such as ether sulfates, e.g., REWOPOL® [2] NL 3, ether carboxylates such as REWOPOL® CLN 100, sulfosuccinates such as REWOPOL® SB FA 30, REWOPOL® SBZ and REWODERM® [3] SPS, nonionic surfactants such as glycerol fatty acid ester ethoxylates, e. g., REWODERM® ES 90, glycerol monostearates, e. g., REWOMUL® [4] MG, and cetyl alcohol [1], [2], [3] and [4]. (Trademarks of REWO Chemische Werke GmbH, Steinau an der Straße).

Along with the inventive compounds, which are used in amounts of from 1 to 10 parts by weight, and preferably from 2 to 8 parts by weight, for shampoos and of from 1 to 7 parts by weight, and preferably from 1 to 5 parts by weight, for creams, the other surfactants are generally used in amounts of from 1 to 20 parts by weight, and preferably from 1 to 15 parts by weight, for shampoos and of from 1 to 10 parts by weight, and preferably from 2 to 5 parts by weight, for creams.

As thickeners, from 1 to 8 parts by weight of the compounds generally employed in this field, such as glycerol fatty acid ester ethoxylates, fatty alcohol ethoxylates, fatty acid alkylolamides and the usual alkali-metal, alkaline-earth and ammonium salts, which at 20° C. are soluble in water in amounts of at least 1 weight percent, and particularly NaCl or NH₄Cl, are used.

Analytical methods

Solids content

The solids content is determined by heating and drying the substance to constant weight at 105° C.

Saponification number

The saponification number is a measure of the free and combined acids contained in fats and technical-grade fatty acids. It is the number of milligrams of potassium hydroxide required for the saponification of 1 gram of substance or technical-grade fatty acid (mg KOH/g). These values are determined by the standard methods of Deutsche Gesellschaft für Fettchemie (DGF), DGF C-V3.

Hydroxyl number

The hydroxyl number is a measure of the hydroxyl groups contained in a substance. It is the number of milligrams of potassium hydroxide required for neutralization of the acetic acid consumed by 1 gram of substance during acetylation (mg KOH/g). These values are determined by the standard methods of Deutsche Gesellschaft für Fettchemie (DGF), DGF C-V17a.

Surfactant content

The surfactant content indicated in the examples which follow was determined by the commonly employed two-phase titration with benzalkonium chloride, using methylene blue as indicator. (See S. R. Epton, Nature (London), 160, 795 [1967].)

(A) Examples of syntheses

EXAMPLE 1

Into a laboratory autoclave, 848 g (4.66 mols) of sorbitol is introduced and melted at 100° C. After i g of sodium hydroxide has been added, 410 g (9.32 mols) of ethylene oxide is fed in at a temperature of from 130° to 150° C. so that the pressure in the reaction vessel does not exceed 4 bars. On completion of the reaction, the product has a hydroxyl number of 1,174.

In a 1-liter four-neck flask equipped with stirrer, internal thermometer, inert-gas inlet and distillation head, 270 g (1 mol) of ethoxylated sorbitol is mixed with 0.4 g of tetraisopropyl titanate and, after 235 g (1 mol) of $C_{12}$–$C_{18}$ coco fatty acid methyl ester has been slowly added, heated to 130° C. under a nitrogen atmosphere. The methanol formed is continuously distilled off under normal pressure. Optionally the reaction is caused to go to completion by applying a vacuum. The transesterification product has a hydroxyl number of 575 and a saponification number of 114.

In a 500-ml four-neck flask equipped with stirrer, internal thermometer, inert-gas inlet and reflux condenser, 260 g (0.55 mol) of sorbitol monoester is mixed with 108 g (1.1 mols) of maleic anhydride and heated for 2 hrs at 80°–90° C. under a nitrogen atmosphere. 280 g of the maleic half-ester is then poured into a solution, heated to 70° C., of 111 g of sodium sulfite in 580 ml of water, and stirred at that temperature until the $SO_2$ content of the solution is less than 0.01%. A solution with a solids content of 40.0% and a surfactant content of 25.8% is obtained.

EXAMPLE 2

Into a laboratory autoclave, 414 g (2.27 mols) of sorbitol is introduced and melted at 100° C. After 1 g of sodium hydroxide has been added, 300 g (6.82 mols) of ethylene oxide is fed in at a temperature of from 130° to 150° C. so that the pressure in the reaction vessel does not exceed 4 bars. On completion of the reaction, the product has a hydroxyl number of 1,065.

In a 2-liter four-neck flask equipped with stirrer, internal thermometer, inert-gas inlet and distillation head, 585 g (1.86 mols) of ethoxylated sorbitol is mixed with 2.9 g of potassium carbonate and, after 235 g (1.86 mols) of $C_{12}$–$C_{18}$ coco fatty acid methyl ester has been slowly added, heated to 125° C. under a nitrogen atmosphere. The methanol formed is continuously distilled off under normal pressure. Optionally the reaction is caused to go to completion by applying a vacuum. The transesterification product has a hydroxyl number of 634 and a saponification number of 128.

In a 500-ml four-neck flask equipped with stirrer, internal thermometer, inert-gas inlet and reflux condenser, 207 g (0.4 mol) of sorbitol monoester is mixed with 118 g (1.2 mols) of maleic anhydride and heated for 2 hrs at 80°–90° C. under a nitrogen atmosphere.

280 g of the maleic half-ester is then poured into a solution, heated to 70° C., of 137 g of sodium sulfite in 625 ml of water, and stirred at that temperature until the $SO_2$ content of the solution is less than 0.01%. A solution with a solids content of 43.7% and a surfactant content of 40.6% is obtained.

EXAMPLE 3

In a 500-ml four-neck flask equipped with stirrer, internal thermometer, inert-gas inlet and reflux condenser, 259 g (0.5 mol) of sorbitol monoester from Example 2 is mixed with 98 g (1 mol) of maleic anhydride and heated for 2 hrs at 80°–90° C. under a nitrogen atmosphere.

300 g of the maleic half-ester is then poured into a solution, heated to 70° C., of 111 g of sodium sulfite in 615 ml of water, and stirred at that temperature until the $SO_2$ content of the solution is less than 0.01%. A solution with a solids content of 40.4% and a surfactant content of 28.5% is obtained.

EXAMPLE 4

Into a laboratory autoclave, 520 g (2.85 mols) of sorbitol is introduced and melted at 100° C. After 1 g of sodium hydroxide has been added, 630 g (14.3 mols) of ethylene oxide is fed in at a temperature of from 130° to 150° C. so that the pressure in the reaction vessel does not exceed 4 bars. On completion of the reaction, the product has a hydroxyl number of 818.

In a 1-liter four-neck flask equipped with stirrer, internal thermometer, inert-gas inlet and distillation head, 402 g (1 mol) of ethoxylated sorbitol is mixed with 1.2 g of methanesulfonic acid and, after 220 g (1 mol) of $C_{12}$–$C_{18}$ coco fatty acid has been added, heated to 180° C. under a nitrogen atmosphere. The water of reaction formed is continuously distilled off under normal pressure. Optionally the reaction is caused to go to completion by applying a vacuum. The esterification product has a hydroxyl number of 404 and a saponification number of 96.

In a 500-ml four-neck flask equipped with stirrer, internal thermometer, inert-gas inlet and reflux condenser, 200 g (0.33 mol) of sorbitol monoester is mixed with 65 g (0.66 mol) of maleic anhydride and heated for 2 hrs at 80°–90° C. under a nitrogen atmosphere. 230 g of the maleic half-ester is then poured into a solution, heated to 70° C., of 76 g of sodium sulfite in 460 ml of water, and stirred at that temperature until the $SO_2$ content of the solution is less than 0.01%. A clear, pale solution with a solids content of 40.0% and a surfactant content of 30.4% is obtained.

EXAMPLE 5

Into a laboratory autoclave, 457 g (2.51 mols) of sorbitol is introduced and melted at 100° C. After 1 g of sodium hydroxide has been added, 728 g (12.6 mols) of propylene oxide is fed at a temperature of from 130° to 150° C. so that the pressure in the reaction vessel does not exceed 4 bars. On completion of the reaction, the product has a hydroxyl number of 705.

In a 1-liter four-neck flask equipped with stirrer, internal thermometer, inert-gas inlet and distillation bridge, 472 g (1 mol) of sorbitol propoxylate is mixed with 2.5 g of potassium carbonate and, after 235 g (1 mol) of $C_{12}$–$C_{18}$ coconut acid methyl ester has been added, heated to 180° C. under a nitrogen atmosphere. The methanol formed is continuously distilled off under normal pressure. Optionally the reaction is caused to go to completion by applying a vacuum. The transesterification product has a hydroxyl number of 380 and a saponification number of 78.

In a 500-ml four-neck flask equipped with stirrer, internal thermometer, inert-gas inlet and reflux condenser, 270 g (0.4 mol) of sorbitol monoester is mixed with 118 g (1.2 mols) of maleic anhydride and heated for 2 hrs at 80°–90° C. under a nitrogen atmosphere. 340 g of the maleic half-ester is then poured into a solution, heated to 70° C., of 140 g of sodium sulfite in 720 ml of water, and stirred at that temperature until the $SO_2$ content of the solution is less than 0.01%. A clear, bright solution with a solids content of 40.1% and a surfactant content of 19.2% is obtained.

EXAMPLE 6

Into a laboratory autoclave, 394 g (2.16 mols) of sorbitol is introduced and melted at 100° C. After 1 g of sodium hydroxide has been added, 950 g (21.6 mols) of ethylene oxide is fed in at a temperature of from 130° to 150° C. so that the pressure in the reaction vessel does not exceed 4 bars. On completion of the reaction, the product has a hydroxyl number of 518.

In a 1-liter four-neck flask equipped with stirrer, internal thermometer, inert-gas inlet and distillation head, 373 g (0.6 mol) of ethoxylated sorbitol is mixed with 2 g of potassium carbonate and, after 141 g (0.6 mol) of $C_{12}$–$C_{18}$ coco fatty acid methyl ester has been slowly added, heated to 130° C. under a nitrogen atmosphere. The methanol formed is continuously distilled off under normal pressure. Optionally the reaction is caused to go to completion by applying a vacuum. The transesterification product has a hydroxyl number of 315 and a saponification number of 61.

In a 500-ml four-neck flask equipped with stirrer, internal thermometer, inert-gas inlet and reflux condenser, 206 g (0.25 mol) of sorbitol monoester is mixed with 49 g (0.5 mol) of maleic anhydride and heated over 2 hr. to 80°–90° C. under a nitrogen atmosphere. 204 g of the maleic half-ester is then poured into a solution, heated to 70° C., of 53 g of sodium sulfite in 390 ml of water, and stirred at that temperature until the $SO_2$ content of the solution is less than 0.01%. A solution with a solids content of 40.2% and a surfactant content of 33.1% is obtained.

EXAMPLE 7

In a 1-liter four-neck flask equipped with stirrer, internal thermometer, inert-gas inlet and distillation head, 689 g (1.11 mols) of ethoxylated sorbitol from Example 6 is mixed with 3.4 g of potassium carbonate and, after 390 g (1.66 mols) of $C_{12}$–$C_{18}$ coco fatty acid methyl ester has been slowly added, heated to 130° C. under a nitrogen atmosphere. The methanol formed is continuously distilled off under normal pressure. Optionally the reaction is caused to go to completion by applying a vacuum. The transesterification product has a hydroxyl number of 271 and a saponification number of 87.

In a 500-ml four-neck flask equipped with stirrer, internal thermometer, inert-gas inlet and reflux condenser, 278 g (0.3 mol) of sorbitol monoester is mixed with 88 g (0.9 mol) of maleic anhydride and heated for 2 hrs at 80°–90° C. under a nitrogen atmosphere. 330 g of the maleic half-ester is then poured into a solution, heated to 70° C., of 108 g of sodium sulfite in 660 ml of water, and stirred at that temperature until the $SO_2$ content of the solution is less than 0.01%. A solution with a solids content of 39.0% and a surfactant content of 34.3% is obtained.

EXAMPLE 8

In a 500-ml four-neck flask equipped with stirrer, internal thermometer, inert-gas inlet and reflux condenser, 370 g (0.4 mol) of the sorbitol monoester from Example 6 is mixed with 39 g (0.4 mol) of maleic anhydride and heated for 2 hrs at 80°–90° C. under a nitrogen atmosphere. 375 g of the maleic half-ester is then poured into a solution, heated to 70° C., Of 49 g Of sodium sulfite in 640 ml of water, and stirred at that temperature until the $SO_2$ content of the solution is less than 0.01%. A solution with a solids content of 39.6% and a surfactant content of 23.9% is obtained.

EXAMPLE 9

Into a laboratory autoclave, 394 g (2.16 mols) of sorbitol is introduced and melted at 100° C. After 1 g of sodium hydroxide has been added, 1,900 g (43.2 mols) of ethylene oxide is fed in at a temperature of from 130° to 150° C. so that the pressure in the reaction vessel does not exceed 4 bars. On completion of the reaction, the product has a hydroxyl number of 314.

In a 1-liter four-neck flask equipped with stirrer, internal thermometer, inert-gas inlet and distillation head, 425 g (0.4 mol) of ethoxylated sorbitol is mixed with 2 g of potassium carbonate and, after 94 g (0.4 mol) of $C_{12}$–$C_{18}$ coco fatty acid methyl ester has been slowly added, heated to 130° C. under a nitrogen atmosphere. The methanol formed is continuously distilled off under normal pressure. Optionally the reaction is caused to go to completion by applying a vacuum. The transesterification product has a hydroxyl number of 207 and a saponification number of 43.

In a 500-ml four-neck flask equipped with stirrer, internal thermometer, inert-gas inlet and reflux condenser, 253 g (0.2 mol) of sorbitol monoester is mixed with 39 g (0.4 mol) of maleic anhydride and heated for 2 hrs at 80°–90° C. under a nitrogen atmosphere. 249 g of the maleic half-ester is then poured into a solution, heated to 70° C., of 45 g of sodium sulfite in 440 ml of water, and stirred at that temperature until the $SO_2$ content of the solution is less than 0.01%. A solution with a solids content of 40.0% and a surfactant content of 36.9% is obtained.

EXAMPLE 10

In a 1-liter four-neck flask equipped with stirrer, internal thermometer, inert-gas inlet and distillation head, 242 g (0.23 mol) of ethoxylated sorbitol from Example 9 is mixed with 1.2 g of potassium carbonate and, after 107 g (0.46 mol) of $C_{12}$–$C_{18}$ coco fatty acid methyl ester has been slowly added, heated to 130° C. under a nitrogen atmosphere. The methanol formed is continuously distilled off under normal pressure. Optionally the reaction is caused to go to completion by applying a vacuum. The transesterification product has a hydroxyl number of 142 and a saponification number of 73.

In a 500-ml four-neck flask equipped with stirrer, internal thermometer, inert-gas inlet and reflux condenser, 293 g (0.2 mol) of sorbitol monoester is mixed with 39 g (0.4 mol) of maleic anhydride and heated for 2 hrs at 80°–90° C. under a nitrogen atmosphere. 300 g of the maleic half-ester is then poured into a solution, heated to 70° C., of 48 g of sodium sulfite in 520 ml of water, and stirred at that temperature until the $SO_2$ content of the solution is less than 0.01%. A solution with a solids content of 39.9% and a surfactant content of 28.8% is obtained.

EXAMPLE 11

Into a laboratory autoclave, 523 g (3.44 mols) of xylitol is introduced and melted at 100° C. After 1 g of sodium hydroxide has been added, 757 g (17.2 mols) of ethylene oxide is fed in at a temperature of from 150° to 180° C. so that the pressure in the reaction vessel does not exceed 4 bars. On completion of the reaction, the product has a hydroxyl number of 735.

In a 1-liter four-neck flask equipped with stirrer, internal thermometer, inert-gas inlet and distillation head, 372 g (1 mol) of ethoxylated xylitol is mixed with 1.8 g of potassium carbonate and, after 235 g (1 mol) of $C_{12}$–$C_{18}$ coco fatty acid methyl ester has been slowly added, heated to 130° C. under a nitrogen atmosphere. The methanol formed is continuously distilled off. Optionally the reaction is caused to go to completion by applying a vacuum. The transesterifcation product has a hydroxyl number of 381 and a saponification number of 95.

In a 500-ml four-neck flask equipped with stirrer, internal thermometer, inert-gas inlet and reflux condenser, 247 g (0.43 mol) of xylitol monoester is mixed with 105 g (1.1 mols) of maleic anhydride and heated for 2 hrs at 80°–90° C. under a nitrogen atmosphere. 300 g of the maleic half-ester is then poured into a solution, heated to 70° C., of 121 g of sodium sulfite in 630 ml of water, and stirred at that temperature until the $SO_2$ content of the solution is less than 0.01%. A solution with a solids content of 45.2% and a surfactant content of 40.0% is obtained.

EXAMPLE 12

Into a laboratory autoclave, 261 g (1.72 mols) of xylitol is introduced and melted at 100° C. After 1 g of sodium hydroxide has been added, 757 g (17.2 mols) of ethylene oxide is fed in at from 150° to 180° C. so that the pressure in the reaction vessel does not exceed 4 bars. On completion of the reaction, the product has a hydroxyl number of 470.

In a 1-liter four-neck flask equipped with stirrer, internal thermometer, inert-gas inlet and distillation head, 414 g (0.7 mol) of ethoxylated xylitol is mixed with 2 g of potassium carbonate and, after 165 g (0.7 mol) of $C_{12}$–$C_{18}$ coco fatty acid methyl ester has been slowly added, heated to 130° C. under a nitrogen atmosphere. The methanol formed is continuously distilled off under normal pressure. Optionally the reaction is caused to go to completion by applying a vacuum. The transesterification product has a hydroxyl number of 284 and a saponification number of 68.

In a 1-liter four-neck flask equipped with stirrer, internal thermometer, inert-gas inlet and reflux condenser, 518 g (0.4 mol) of xylitol monoester is mixed with 78 g (0.8 mol) of maleic anhydride and heated for 2 hrs at 80°–90° C. under a nitrogen atmosphere. 350 g of the maleic half-ester is then poured into a solution, heated to 70° C., of 94 g of sodium sulfite in 660 ml of water, and stirred at that temperature until the $SO_2$ content of the solution is less than 0.01%. A solution with a solids content of 39.8% and a surfactant content of 34.6% is obtained.

Coding of surfactants used (CTFA nomenclature)

1 = Disodium PEG-4 Cocamido MIPA-Sulfosuccinate
2 = Disodiumlauroamphodiacetate (and) Sodium Lauryl Sulfate (and) Hexylene Glycol
3 = Cocoamidopropyl Hydroxysultaine
4 = Ricinoleamidopropyltrimonium Methosulfate
5 = PEG-200 Glyceryl Tallowate mod.
6 = Disodium Laureth Sulfosuccinate
7 = Sodium Laureth Sulfate
8 = Cocoamidopropyl Betaine
9 = PEG-200 Glyceryl Tallowate
10 = Disodiumcocoamphodiacetate
11 = PEG-80 Glyceryl Tallowate
12 = Cocoamidopropyl Betaine
13 = Glyceryl Stearate
14 = Laureth-6

Test methods

Hard-water compatibility: DIN 53 905
Skin Compatibility (zein test):
Götte, Ernst, Chem. Phys. Appl. Surface-Active Subst. Proc. Int. Congr. 4 ( 1964 ) 83–90:
<200 mqN/100 ml = non irritant
200–400 mqN/100 ml = slightly irritant
>400 mqN/100 ml = irritant
Surface tension:
Dr. R. Hensch, Fette, Seifen, Anstrichmittel 72 (1970), pp. 969–977.
Viscosity:
Brookfield Viscometer (cup and spindle), measured at 20° C. as specified by manufacturer.

Foaming power determined according to Ross Miles on the of DIN 53 902, Part 2, except for the following dimensions and quantities:

| | |
|---|---|
| Inside diameter of discharge nozzle: | 3.5 mm |
| Height of fall of test solution: | 940 mm |
| Quantity of test solution initially introduced: | 50 ml |
| Quantity of in-flowing test solution: | 200 ml |

TABLE 1

| Example | a + b + c + d | e | R | $R^1$ | $R^2$ | $R^2$ | $R^2$ |
|---|---|---|---|---|---|---|---|
| 1  | 2 EO  | 3 | $C_{11}/C_{17}$ | H | H | H | H |
| 2  | 3 EO  | 3 | $C_{11}/C_{17}$ | H | Sulfosuccinate | Sulfosuccinate | H |
| 3  | 3 EO  | 3 | $C_{11}/C_{17}$ | H | Sulfosuccinate | Sulfosuccinate | H |
| 4  | 5 EO  | 3 | $C_{11}/C_{17}$ | H | Sulfosuccinate | Sulfosuccinate | H |
| 5  | 5 PO  | 3 | $C_{11}/C_{17}$ | H | Sulfosuccinate | Sulfosuccinate | H |
| 6  | 10 EO | 3 | $C_{11}/C_{17}$ | H | Sulfosuccinate | H | H |
| 7  | 10 EO | 3 | $C_{11}/C_{17}$ | $C_{11}/C_{17}$* | Sulfosuccinate | Sulfosuccinate | H |
| 8  | 10 EO | 3 | $C_{11}/C_{17}$ | H | H | H | H |
| 9  | 20 EO | 3 | $C_{11}/C_{17}$ | H | Sulfosuccinate | H | H |
| 10 | 20 EO | 3 | $C_{11}C_{17}$ | $C_{11}/C_{17}$* | Sulfosuccinate | H | H |
| 11 | 5 EO  | 2 | $C_{11}/C_{17}$ | H | Sulfosuccinate | Sulfosuccinate | H |
| 12 | 10 EO | 2 | $C_{11}/C_{17}$ | H | Sulfosuccinate | H | H |

*) Alkyl group or alkylene group of corresponding acid (B) End-use testing

The formulations which follow can be prepared simply by stirring the ingredients of the formulation into water.

All formulations are given in percent by weight of solid.

| | | |
|---|---|---|
| Measuring temperature: | 40° C | |
| Solvent: | Demineralized water | |
| Basic formula: Skin cleanser and makeup remover for sensitive skin | | |
| Inventive compound | 2–8 | parts by weight |
| REWOTERIC ®* AM B 14(12) | 2–8 | " |
| Hydroxyethylcellulose | 0.2–1.5 | " |

-continued

| Basic formula: Skin cream | |
|---|---|
| Demineralized water | Enough to make 100 " |
| Inventive compound | 1-5 parts by weight |
| Glycerol monostearate | 2-10 " |
| Cetyl alcohol | 1-4 " |
| Paraffin oil 3.5° E | 4-12 " |
| Glycerol | 1-5 " |
| Demineralized water | Enough to make 100 " |
| Preservative | As needed |

Basic formula: dishwashing agent

| Inventive compound | 1-5 parts by weight |
|---|---|
| REWOPOL ®* NL 3-28[7] | 1-30 " |
| REWOTERIC ® AM CAS[3] | 1-5 " |
| REWOPAL ® LA 6[14] | 1-10 " |
| Demineralized water | Enough to make 100 " |

Basic formula: Shower bath

| Inventive compound | 2-8 parts by weight |
|---|---|
| REWOTERIC ® AM G 30[2] | 5-15 " |
| REWOTERIC ® AM CAS[3] | 2-6 " |
| REWOQUAT ®* RTM 50[4] | 1-3 " |
| REWODERM ®* LI S 75[5] | 1-4 " |
| Demineralized water | Enough to make 100 " |

Basic formula: Hair shampoo

| Inventive compound | 2-8 parts by weight |
|---|---|
| REWOPOL ®* NL 3-28[7] | 4-10 " |
| REWOTERIC ® AM B 13[8] | 2-8 " |
| REWODERM ® LI 420-70[9] | 1-4 " |
| Demineralized water | Enough to make 100 " |

Basic formula: Baby shampoo

| Inventive compound | 2-8 parts by weight |
|---|---|
| REWOTERIC ® AM 2 C NM[10] | 2-8 " |
| REWOTERIC ® AM B 13[8] | 4-12 " |
| REWOPOL ® NL 3-28[7] | 2-10 " |
| REWODERM ® LI 48-50[11] | 1-4 " |
| Demineralized water | Enough to make 100 " |

*) Trademark of REWO Chemie Werke GmbH, Steinau an der Straße

TABLE 2

| Example from Table 1 | Foaming power (mm) Instant | Foaming power (mm) After 5 min. | Compatibility with calcium water hardness Points | Compatibility with calcium water hardness Class | Zein test (mgN/100 ml) | Surface tension Lecomte de Noëy (Ring method) (mN/m) 0.1% | Surface tension Lecomte de Noëy (Ring method) (mN/m) 0.01% |
|---|---|---|---|---|---|---|---|
| Example 4 | 145 | 135 | 75 | V | 26 | 37.4 | 41.3 |
| Example 5 | 110 | 90 | 75 | V | — | 41.9 | 43.4 |
| Example 6 | 125 | 115 | 75 | V | 20 | 42.0 | 43.9 |
| Example 7 | 110 | 100 | 75 | V | 32 | 40.7 | 47.4 |
| Example 9 | 125 | 110 | 75 | V | 18 | 41.3 | 44.8 |
| Example 10 | 100 | 60 | 75 | V | 28 | 44.9 | 49.9 |
| Example 11 | 120 | 110 | 75 | V | — | 35.7 | 43.9 |
| Example 12 | 125 | 110 | 75 | V | 23 | 38.8 | 41.1 |
| Comparative example REWOPOL ® NL 3-28[1] | 200 | 180 | 75 | V | 300 | 34.2 | 32.9 |
| Comparative example REWOPOL ® SB FA 30[2] | 170 | 160 | 75 | V | 250 | 28.0 | 31.4 |

CFTA nomenclature:
[1] = Consecutive No. 7
[2] = Consecutive No. 6

Test formula: Shower bath

The examples in accordance with the invention were evaluated in a test formula by a test panel of 20 persons (female and male) with respect to
foaming power,
skin feeling, and
skin feeling of dried skin.
Skin compatibility Reduction of the zein values in the formula of Table 4.

TABLE 3

| Formula | 1 | 2 | 3 |
|---|---|---|---|
| Example 4 | — | 4 | — |
| Example 10 | — | — | 4 |
| REWOPOL ® SB Z[1] | 4 | — | — |
| REWOTERIC ® AM G 30[2] | 10.5 | 10.5 | 10.5 |
| REWOTERIC ® AM CAS[3] | 3 | 3 | 3 |
| REWOQUAT ® RTM 50[4] | 1 | 1 | 1 |
| REWODERM ® LI S 75[5] | 2.3 | 2.3 | 2.3 |
| Demineralized water: Sufficient to make | 100 pts. | 100 pts. | 100 pts. |
| pH value, adjusted with citric acid | 6.5 | 6.5 | 6.5 |
| Viscosity, adjusted with NaCl (mPas) | ca. 1000 | ca. 1000 | ca. 1000 |
| Foam height (mm) | 195/185 | 195/180 | 190/185 |
| Foaming initial performance[A] | Good | Good | Good |
| Foam structure[A] | Fine bubbles | Creamy, fine bubbles | Creamy, fine bubbles |
| skin feeling wet skin[A] | Relatively smooth | Smooth | Smooth |
| skin feeling dried skin[A] | Relatively smooth | Smooth | Smooth |

[A] The evaluation was done by means of a graded rating system, with the above ratings representing the arithmetic mean.

Initial Foaming performance: Determination of the amount of foam produced by rubbing the preparation between the wet hands, as in washing the hands.

TABLE 4

Test formula: Skin-cleansing preparation. Reduction of zein values.

| | 1 | 2 | 3 |
|---|---|---|---|
| Example 6 | 4.5 | — | — |
| REWOPOL ® SB FA 30[6] | — | 4.5 | — |
| REWOPOL ® NL 3-28[7] | 10.5 | 10.5 | 15 |
| Demineralized water | 85 | 85 | 85 |
| pH value, adjusted with citric acid | 6.5 | 6.5 | 6.5 |
| Evaluation of foam quality | Creamy, fine bubbles | Fine bubbles | Coarse bubbles |
| Skin feeling after washing, dried skin | Pleasantly smooth | Soft | Somewhat rough |
| Skin compatibility zein values | 104 mgN/ 100 ml | 270 mgN/ 100 ml | 300 mgN/ 100 ml |

Test formula: Hair shampoo

The examples in accordance with the invention were evaluated in the form of this formula with respect to ease of combing and hair volume and set of hair style by ten test persons with experience in shampoo application.

TABLE 5

| Formula | 1 | 2 |
|---|---|---|
| Example 6 | — | 3 |
| REWOPOL ® NL 3-28[7] | 8 | 6 |
| REWOTERIC ® AM B 13[8] | 5 | 4 |
| REWODERM ® LI 420-70[9] | 2.1 | 2.1 |
| Demineralized water: Sufficient to make | 100 parts | 100 parts |
| pH value, adjusted with citric acid | 6.5 | 6.5 |
| Viscosity, adjusted with sodium chloride (mPas) | ca. 1000 | ca. 1000 |
| Ease of combing | 3 | 5-6 |
| hair volume | 3-4 | 6 |
| Set of hair style | | |
| Foaming power (mm) | 195/185 | 190/185 |

Rating of ease of combing 1-3 = Combing is difficult. The hair offers considerable resistance to combing.
4-7 = Combing is fairly easy. Resistance to combing is lower, adequate for a conditioning shampoo, depending on the hair type.
8-10 = Reserved for the later after treatment with hair rinses.

Rating of hair volume and of hair style 1-3 = Hair is dry or stringy (straw like); poor set of hair style.
4-7 = Hair is soft and with full body, with good set of hair style.
8-10 = Hair is soft and smooth but too loose, hence poor set of hair style.

Ratings based on a point system, with the above ratings representing the arithmetic mean.

Test formula: Baby shampoo, or hair and body shampoo for sensitive skin

TABLE 6

| Formula | 1 | 2 | 3 |
|---|---|---|---|
| Example 6 | — | 3 | — |
| Example 10 | — | — | 3 |
| REWOTERIC ® AM 2 C NM[10] | 3.5 | 3.5 | 3.5 |
| REWOTERIC ® AM B 13[8] | 7 | 7 | 7 |
| REWOPOL ® NL 3-28[7] | 7.5 | 4.5 | 4.5 |
| REWODERM ® LI 48-50[11] | 3 | 3 | 3 |
| Demineralized water: Sufficient to make | 100 pts. | 100 pts. | 100 pts. |
| pH value, adjusted with citric acid | 6.5 | 6.5 | 6.5 |
| Foaming power (mm) | 195/185 | 195/185 | 195/185 |
| Skin compatibility zein values (mgN/100 ml) | ~70 | ~30 | ~30 |
| Foam structure | Coarse bubbles | Fine bubbles | Fine bubbles |
| Skin feeling wet and dried skin | Somewhat rough | Smooth Soft | Smooth Soft |

Test formula: Skin Cleanser and makeup remover for sensitive skin

TABLE 7

| Formula | 1 | 2 |
|---|---|---|
| Example 6 | — | 4 |
| REWOPOL ® SB FA 30[6] | 4 | — |
| REWOTERIC ® AM B 14[12] | 4.5 | 4.5 |
| Hydroxyethylcellulose | 0.5 | 0.5 |
| Demineralized water: Sufficient to make | 100 parts | 100 parts |
| pH value, adjusted with citric acid | 6.5 | 6.5 |
| Skin compatibility zein values (mgN/100 ml) | ca. 170 | <50 |

The use of the inventive sulfosuccinates in this formula results in a cleaning agent that is readily tolerated by the skin, as evidenced by the low zein value compared to the standard sulfosuccinate REWOPOL ® SB FA 30.

TABLE 8

Test formula: O/W skin cream

| Formula | 1 | 2 | 3 | 4 |
|---|---|---|---|---|
| Example 4 | — | — | 2 | — |
| Example 9 | — | — | — | 2 |
| Stearyl alcohol, ethoxylated (3 EO) | 2 | — | — | — |
| REWOMUL ® MG 13[13] | 6 | 6 | 6 | 6 |
| REWOPOL ® SB FA 30[6] | — | 2 | — | — |
| Cetyl alcohol | 2 | 2 | 2 | 2 |
| Paraffin oil 3.5° E | 8 | 8 | 8 | 8 |
| Glycerol | 3 | 3 | 3 | 3 |
| Preservative | As needed | As needed | As needed | As needed |
| Demineralized water: Sufficient to make | 100 parts | 100 parts | 100 parts | 100 parts |
| Stability of emulsion at 5°, 20° and 40° C. | Stable | Unstable | Stable | Stable |
| Appearance | Smooth, white cream | Gritty; emulsion breaks | Smooth, white cream | Smooth, white cream |

In an evaluation Of the skin-contact Properties by ten test persons, more than 80 percent rated the test formulas 3 and 4 as
   easy to spread on the skin;
   readily absorbed by the skin; and
   making the skin soft and smooth without being sticky or greasy.

Comparative formula 1 was rated the same. Formula 2 is unstable.

TABLE 9

| Test formula: Nonirritating hand dish-washing agent | | | | |
|---|---|---|---|---|
| Formula | 1 | 2 | 3 | 4 |
| Example 6 | — | 3 | 1.5 | — |
| REWOPOL ® NL 3-28[7] | 18 | 18 | 18 | 18 |
| REWOTERIC ® AM CAS[3] | 1.5 | — | 1.5 | — |
| REWOPAL ® LA 6[4] | 1.5 | — | 1.5 | 3 |
| Demineralized water: Sufficient to make | 100 parts | 100 parts | 100 parts | 100 parts |
| Viscosity (mPa · s), adjusted with NaCl to ca. | 500 | 500 | 500 | 500 |
| Foaming power (mm) | 195/185 | 195/180 | 195/185 | 190/180 |
| +0.5 ml olive oil | 190/180 | 185/180 | 190/180 | 190/180 |
| +1.0 ml olive oil | 190/185 | 180/175 | 190/180 | 190/180 |
| Skin compatibility zein values (mgN/100 ml) | 220 | 220 | 190 | 250 |

We claim:

1. A fatty acid polyol polyether sulfosuccinate of the general formula

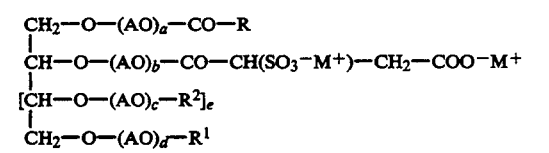

(I)

wherein
R is a straight-chain or branched-chain alkyl or alkylene group having from 7 to 21 carbon atoms;
$R^1$ is H or —CO—R;
$R^2$ is independently of each other, H or —CO—CH($SO_3^{-}M^+$)—$CH_2$—$COO^-M^+$;
A is the same or different and each is an alkylene group having from 2 to 3 carbon atoms;
a,b,c and d are the same or different, and each is from 0 to 5,
e is from 1 to 3,
f is a multiplication product of c times e, and a+b+f+d is from 2 to 25; and
$M^+$ is an alkali-metal ion or an ammonium ion.

2. The fatty acid polyol polyether sulfosuccinate as claimed in claim 1, wherein
R is a straight-chain or branched-chain alkyl or alkylene group having from 11 to 17 carbon atoms;
$R^2$ is, independently of each other, H or the group —CO—CH($SO_3^-Na^+$)—$CH_2$—$COO^-Na^+$;
AO is ethylene oxide, propylene oxide or ethylene oxide and propylene oxide;
a,b,c, and d are the same or different, and each is from 1 to 3, a+b+f+d is from 5 to 20,
e is 3; and
$M^+$ is $Na^+$.

3. The fatty acid polyol polyether sulfosuccinate as claimed in claim 2, wherein a+b+f+d is from 5 to 10 and $R^1$ and $R^2$ are each a moiety of a fatty acid wherein the fatty acid is selected from the group consisting of coconut acid, oleic acid, ricinoleic acid, lauric acid and mixtures thereof.

4. A process for preparing compounds of the general formula

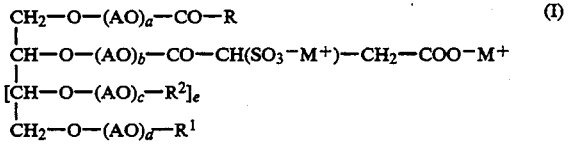

(I)

wherein
R is a straight-chain or branched-chain alkyl or alkylene group having from 7 to 21 carbon atoms;
$R^1$ is H or —CO—R;
$R^2$ is, independently of each other, H or the group —CO—CH($SO_3^-M^+$)—$CH_2$—$COO^-M^+$;
A is the same or different and each is an alkylene group having from 2 to 3 carbon atoms;
a,b,c and d are the same or different, and each is from 0 to 5,
e is from 1 to 3,
f is a multiplication product of c times e, and a+b+f+d is from 2 to 25; and
$M^+$ is an alkali-metal ion or an ammonium ion, comprising reacting, in a first step, polyol compounds of the general formula

(II)

with alkylene oxides in the presence of a basic catalyst at temperatures of from 120° to 180° C. under a pressure of not more than 4 bars to give resulting compounds of the general formula

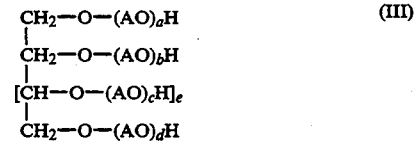

(III)

the molar ratio of polyol to alkylene oxide being between 5 and 20, reacting the resulting compounds of the general formula (III) with fatty acids or fatty acid esters in the presence of a catalyst at temperatures ranging from 120° to 180° C. to give compounds of the general formula

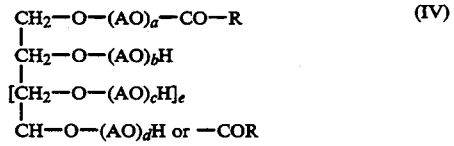

(IV)

reacting these compounds of the general formula (IV) with maleic anhydride at temperatures ranging from 60° to 80° C. to give half-esters, and sulfonating the half-esters with an aqueous sodium sulfite solution to give the compounds of the general formula

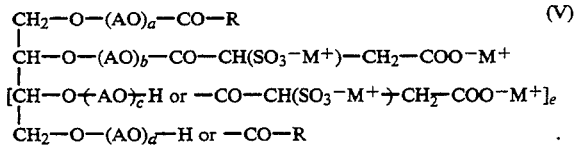

5. The process for preparing compounds of the general formula (I) as claimed in claim 4, wherein ethylene oxide, propylene oxide or both are used as alkylene oxides in amounts of from 5 to 20 mols per mol of polyol, and straight-chain saturated compounds, unsaturated compounds or both, having from 11 to 17 carbon atoms in the hydrocarbon group, are used as fatty acids or fatty acid esters in a molar ratio of 1–2:1 to alkoxylated polyol, and maleic anhydride is used in a molar ratio of 1–3:1 to polyol alkoxylate ester.

* * * * *

UNITED STATES PATENT AND TRADEMARK OFFICE
CERTIFICATE OF CORRECTION

PATENT NO.    : 5,371,251

DATED         : December 6, 1994

INVENTOR(S)   : Hamann et al.

It is certified that error appears in the above-identified patent and that said Letters Patent is hereby corrected as shown below:

On the title page: Item [73] Assignee insert --Rewo Chemische Werke GmbH-- instead of "Witco GmbH".

Signed and Sealed this

Twenty-sixth Day of September, 1995

*Attest:*

BRUCE LEHMAN

*Attesting Officer*     *Commissioner of Patents and Trademarks*